(12) United States Patent
Son et al.

(10) Patent No.: US 10,072,215 B2
(45) Date of Patent: Sep. 11, 2018

(54) DYE-SENSITIZED $TIO_2$ HYBRID SYSTEM WITH RHENIUM AND COBALT CATALYSTS FOR PRODUCING HYDROGEN/CARBON MONOXIDE SYNGAS

(71) Applicant: KOREA UNIVERSITY RESEARCH AND BUSINESS FOUNDATION, SEJONG CAMPUS, Sejong-si (KR)

(72) Inventors: Ho-Jin Son, Gyeonggi-do (KR); Sang Ook Kang, Sejong-si (KR); Jong-Su Lee, Seoul (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 0 days.

(21) Appl. No.: 15/730,068

(22) Filed: Oct. 11, 2017

(65) Prior Publication Data

US 2018/0171236 A1    Jun. 21, 2018

(30) Foreign Application Priority Data

Dec. 16, 2016 (KR) .................. 10-2016-0172434

(51) Int. Cl.
*C10G 2/00* (2006.01)
*B01J 23/889* (2006.01)
*C07C 1/10* (2006.01)
*C07C 1/12* (2006.01)
*C01B 3/00* (2006.01)
*C01G 23/04* (2006.01)

(52) U.S. Cl.
CPC .......... *C10G 2/332* (2013.01); *B01J 23/8896* (2013.01); *C01B 3/00* (2013.01); *C07C 1/10* (2013.01); *C07C 1/12* (2013.01); *C01G 23/04* (2013.01); *C07C 2523/75* (2013.01)

(58) Field of Classification Search
CPC ...................................................... C10G 2/332
USPC ............................................................ 502/300
See application file for complete search history.

(56) References Cited

PUBLICATIONS

Photocatalytic H2 evolution from neutral water with a molecular cobalt catalyst on a dye-sensitized TiO2 nanoparticle. Fezile Lakadamyali et al. Chem. Commun., vol. 47, pp. 1695-1697, (Year: 2011).*
A review of catalysts for the electroreduction of carbon dioxide to produce low-carbon fuels. Jinli Qiao et al. Chem. Soc. Rev. vol. 43, pp. 631675 (Year: 2014).*
Photochemical generation of carbon monoxide and hydrogen by reduction of carbon dioxide and water under visible light irradiation. Jean-Marie Lehn et al. Proc. Natl. Acad. Sci. USA, vol. 79, pp. 701-704 (Year: 1982).*

(Continued)

*Primary Examiner* — Douglas B Call
(74) *Attorney, Agent, or Firm* — Harness, Dickey & Pierce, P.L.C.

(57) ABSTRACT

Disclosed is a hybrid catalyst system for the production of hydrogen/carbon monoxide syngas. The hybrid catalyst system includes a dye, a rhenium (Re) catalyst, and a cobalt (Co) catalyst grafted on a semiconductor metal oxide. The hybrid catalyst system can produce syngas without the aid of external energy and enables control over the ratio of hydrogen/carbon monoxide formed. Therefore, the hybrid catalyst system can find application in various industrial fields, including chemical fuel production.

9 Claims, 16 Drawing Sheets

(56) References Cited

PUBLICATIONS

Lakadamyali, F., et al. (2011) "Photocatalytic $H_2$ evolution from neutral water with a molecular cobalt catalyst on a dye-sensitised $TiO_2$ nanoparticle." *Chem. Commun.*, 47:1695-1697.

Lee, JS., et al. (2017) "Widely controllable syngas production by a dye-sensitized $TiO_2$ hybrid system with $Re^I$ and $Co^{III}$ catalysts under visible-light irradiation." *Angew. Chem. Int. Ed.*, 56:976-980.

Won, Di., et al. (2015) "Highly robust hybrid photocatalyst for carbon dioxide reduction: tuning and optimization of catalytic activities of Dye/$TiO_2$/Re(I) Organic-Inorganic Ternary Systems." *J. Am. Chem. Soc.*, 137:13679-13690.

\* cited by examiner

DYE-SENSITIZED TIO$_2$ HYBRID SYSTEM WITH RHENIUM AND COBALT CATALYSTS FOR PRODUCING HYDROGEN/CARBON MONOXIDE SYNGAS

CROSS REFERENCES TO RELATED APPLICATIONS

The present application claims the benefit and priority to Korean Patent Application No. 10-2016-0172434, filed in the Korean Patent Office on Dec. 16, 2016. The entire disclosure of the application is incorporated herein by reference.

FIELD

The present invention relates to a hybrid catalyst system in which a dye, a rhenium (Re) catalyst, and a cobalt (Co) catalyst are grafted on a semiconductor metal oxide. More specifically, the present invention relates to a hybrid catalyst system for producing hydrogen/carbon monoxide syngas including a dye, a rhenium (Re) catalyst, and a cobalt (Co) catalyst grated on TiO$_2$.

BACKGROUND

Due to the global climate crisis brought by the continuous increase of CO$_2$ emission in the atmosphere (BP statistical Review of World Energy June 2016), the utilization of CO$_2$ as a carbon resource is an important subject in the science and industry fields. The reduction of CO$_2$ to utilizable C1 resources is a major research target in chemical conversions of solar energy, together with the hydrogen evolution by water reduction, to provide a strategic way responding the energy and environmental problems (I. Willner et al., J. Am. Chem. Soc., 109:6080-6, 1987). Among visible-light induced multi-electron reductions of CO$_2$, the two-electron reduction to CO is a kinetically favourable choice because of the relatively low reaction barrier compared to one-electron and other higher-reduction reactions (A. J. V. Underwood, Ind. Eng. Chem., 32:449-54. 1940). Moreover, CO is currently utilized as a carbon source for the production of chemicals in petroleum chemical industry, particularly for the methanol production from a mixture of CO and H$_2$, so-called syngas (M. E. Dry, Catal. Today, 71:227-41, 2002; I. Wender, Fuel Process. Technol., 48:189-297, 1996).

Syngas has been also known as a key feedstock for the production of synthetic bulk chemicals via the Fischer-Tropsch (F-T) processing (A. J. V. Underwood, Ind. Eng. Chem., 32:449-54. 1940). For the production of chemicals from syngas, the tailoring of H$_2$/CO ratio in syngas mixtures is critical, e.g. 2:1 H$_2$/CO for methanol production and F-T hydrocarbon syntheses (M. E. Dry, Catal. Today, 71:227-41, 2002; K. C. Waugh, Catal. Today, 15:51-75, 1992) and 1:1 H$_2$/CO for the production of aldehydes via hydroformylation of alkenes (M. Beller et al., J. Mol. Catal. A: Chem., 104:17-85, 1995). While the simultaneous formation of H$_2$ and CO is known to occur by photochemical and electrochemical reductions of CO$_2$ and water using Ni— (V. S. Thoi et al., J. Am. Chem. Soc., 135:14413-24, 2013), Re— (B. Kumar et al., Chem. Commun., 45:272-4, 2012), and Ru— (P. Kang et al., Energy Environ. Sci., 7:4007-12, 2014)-molecular catalysts, little has been referred to possible control of syngas compositions. Therefore, a new protocol that focuses on adjustability of H$_2$/CO ratio in visible-light induced syngas production should be of scientific significance.

Conventional technologies for catalytic production of syngas require the production of hydrogen and carbon monoxide through independent catalytic conversion processes and mixing of the gases through additional processes. Further, most of the production technologies are limited to the utilization of by-product gases and related processes thereof. Recent technologies for direct production of syngas using molecular catalysts are based on electrochemical methods that still need external energy.

Thus, the present inventors have earnestly and intensively conducted research to develop a method for direct production of syngas without the need for external energy and a catalytic system for producing syngas in which the ratio of gases formed can be controlled, and as a result, found that when two types of transition-metal complex catalysts, i.e. a rhenium catalyst and a cobalt catalyst, are immobilized on TiO$_2$ particles, the resulting catalytic system exhibits high catalytic activity, produces H$_2$ and CO without external energy, and enables control over the ratio of H$_2$/CO formed. The present invention has been accomplished based on this finding.

SUMMARY

It is an object of the present invention to provide a hybrid catalyst system in which a dye, a rhenium (Re) catalyst, and a cobalt (Co) catalyst are grafted on a semiconductor metal oxide.

The present invention provides a hybrid catalyst system for producing hydrogen/carbon monoxide syngas including a dye, a rhenium (Re) catalyst, and a cobalt (Co) catalyst grafted on a semiconductor metal oxide.

The hybrid catalyst system of the present invention can produce syngas without the aid of external energy and enables control over the ratio of gases formed. Therefore, the hybrid catalyst system of the present invention can find application in various industrial fields, including chemical fuel production.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION

Unless defined otherwise, all technical and scientific terms used herein have the same meaning as commonly understood by the ordinary skilled in the art expert. In general, the nomenclature used herein is well-known and commonly used in the art.

Figure 1:
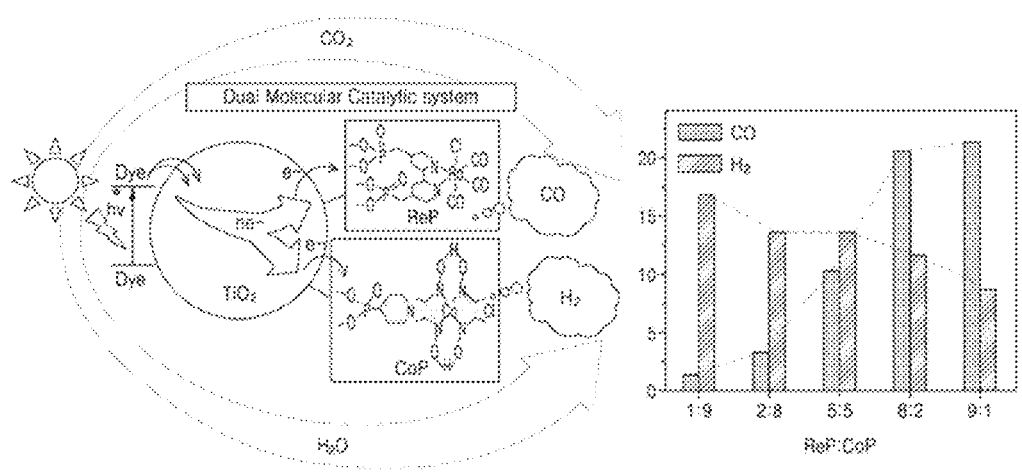
FIG. 1 shows a dye-sensitized TiO$_2$ hybrid system with rhenium and cobalt catalysts (left) and dependences of H$_2$/CO formation on ratios of the catalysts (right)

In one aspect, the present invention is directed to a hybrid catalyst system including a dye, a rhenium (Re) catalyst, and a cobalt (Co) catalyst grafted on a semiconductor metal oxide (FIG. 1).

According to one embodiment of the present invention, the hybrid catalyst system includes a dye, a rhenium (Re) catalyst, and a cobalt (Co) catalyst grafted on $TiO_2$ and is used to produce hydrogen/carbon monoxide syngas from carbon dioxide and water.

In the present invention, the semiconductor metal oxide can receive electrons and transfer the electrons to the rhenium (Re) catalyst or the cobalt (Co) catalyst. The semiconductor metal oxide is preferably $TiO_2$. Other non-limiting examples of semiconductor metal oxides that can be used in the present invention include, but are not limited to, ZnO, $CeO_2$, $C_3N_4$, $ZrO_2$, $SrTiO_2$, $Cu_2O$, Cds, CdSe, and GaP.

In the present invention, the rhenium (Re) catalyst is [fac-[Re(4,4'-bis(diethoxyphosphorylmethyl)-2,2'-bipyridine)$(CO)_3$Cl].

In the present invention, the cobalt (Co) catalyst is [$Co^{II}$-$t$Cl(dimethylglyoximato)$_2$(pyridyl-4-phosphonic acid)].

The hybrid catalyst system of the present invention further includes a sacrificial reagent as an electron donor. The sacrificial reagent is preferably 1,3-dimethyl-2-phenyl-1,3-dihydrobenzimidazole but is not limited thereto.

Figure 2:
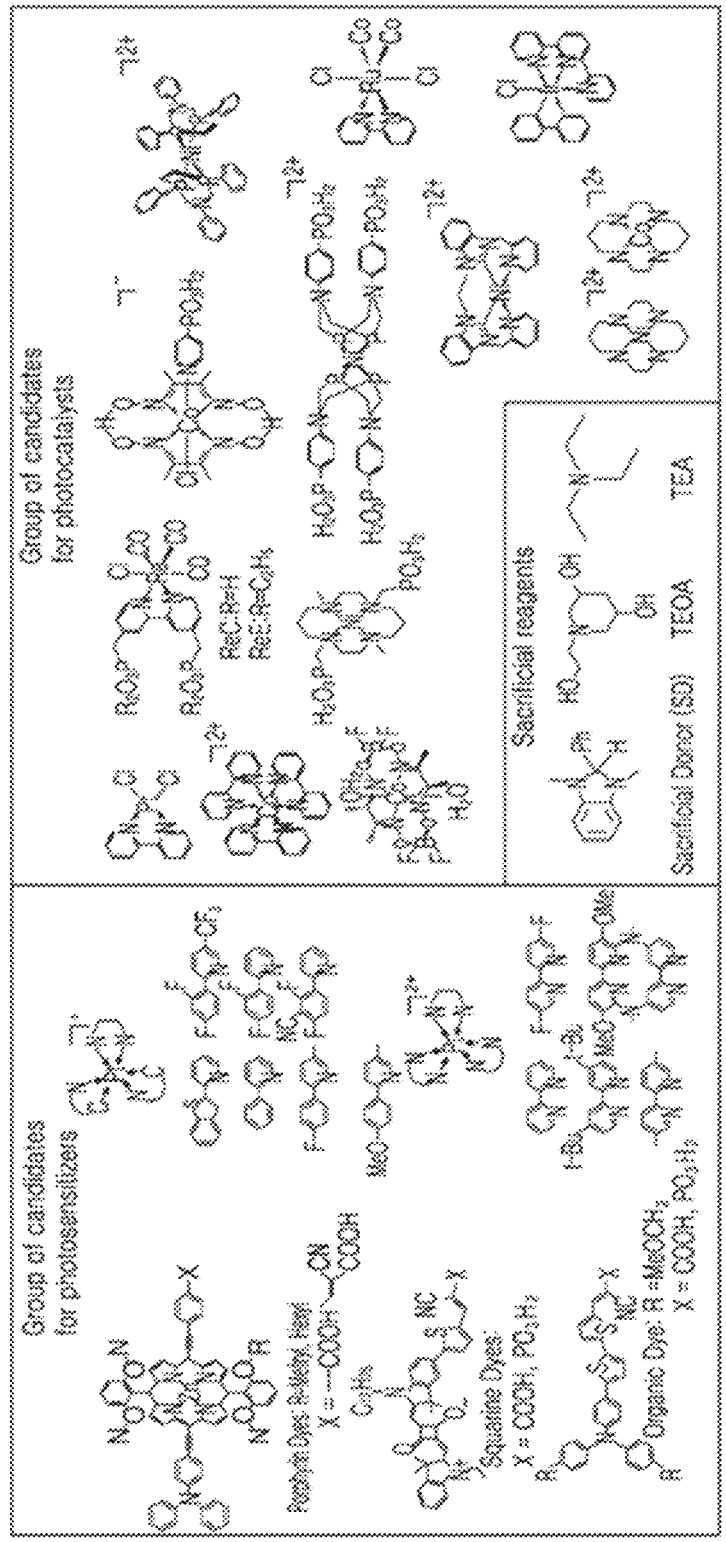
FIG. 2 shows the structures of a group of candidates for photosensitizers, a group of candidates for photocatalysts, and sacrificial reagents that can be used in alternative embodiments of the present invention.

It will be obvious to those skilled in the art that various dyes (photosensitizers), catalysts for carbon monoxide formation based on Ru, Re or Ir, organometallic catalysts, and catalysts for hydrogen formation other than the dye and the catalysts used in the present invention may be used in alternative embodiments of the present invention (FIG. 2).

The hybrid catalyst system of the present invention may further include water. The water content is 20% by volume or less. If the water content exceeds 20% by volume, the electron donor is made insoluble due to the poor solubility of the electron donor in water. Therefore, it is preferred to limit the maximum amount of water to 20% by volume.

The hybrid catalyst system of the present invention produces hydrogen/carbon monoxide syngas and enables control over the ratio of hydrogen/carbon monoxide formed. The molar ratio of hydrogen and carbon monoxide can be controlled from 1:2 to 15:1 by changing the ratio of the rhenium (Re) catalyst and the cobalt (Co) catalyst in the hybrid catalyst system of the present invention, resulting in the production of a wider variety of reactants that can be used in the Fischer-Tropsch reaction.

The hydrogen/carbon monoxide syngas is produced under visible light irradiation. Preferably, the visible light has a wavelength of at least 400 nm. The visible light may be natural light or artificial light.

The present invention will be explained in more detail with reference to the following examples. It will be evident to those skilled in the art that these examples are merely for illustrative purposes and are not to be construed as limiting the scope of the present invention. Therefore, the true scope of the present invention should be defined by the appended claims and their equivalents.

EXAMPLE 1

General Procedures

All reagents were purchased from Aldrich and used without further purification. All manipulations were performed under a dry nitrogen or argon atmosphere by using standard Schlenk techniques. N,N-Dimethylformamide (DMF) was distilled from calcium hydride and stored over molecular sieves. Acetonitrile ($CH_3CN$) was refluxed over and distilled from phosphorus pentoxide ($P_2O_5$) before use. The $^1H$ and $^{13}C$ NMR spectra were recorded on a Varian Mercury 300 spectrometer operating at 300.1 and 75.4 MHz, respectively. The absorption and photoluminescence spectra were recorded on a Shimadzu UV-3101PC UV/Vis/NIR scanning spectrophotometer and on a VARIAN Cary Eclipse fluorescence spectrophotometer, respectively. The diffuse reflectance UV-visible absorption spectra of powder samples were recorded on a Scinco spectrophotometer S-3100. The IR spectra were taken on a Cary 660 FTIR spectrometer. Cyclic voltammetry (CV) measurements were carried out for DMF solutions of rhenium complex, cobalt complex, and Dye (1 mM) in the presence of tetrabutylammonium perchlorate (0.1 M) at room temperature using a BAS 100B electrochemical analyser equipped with a Pt working electrode, a platinum wire counter electrode, and an SCE reference. The Mott-Shottky (MS) measurements were carried out for acetonitrile solutions of the $TiO_2$ working electrode in the presence of tetrabutylammonium perchlorate (0.1 M) at room temperature using a CH Instruments CHI660D equipped with a platinum wire counter electrode and an SCE reference. Particle sizes were determined by a dynamic light scattering technique using a Microtrac UPA 150. Elemental analyses and high resolution tandem mass spectrometry were performed, respectively, on a Carlo Erba Instruments CHNS-O EA 1108 analyzer and on a Jeol LTD JMS-HX 110/110A at the Korean Basic Science Institute (Ochang).

EXAMPLE 2

Preparation of Hybrid $TiO_2$ Catalyst

Commercially available $TiO_2$ particles (Hombikat UV-100) were thoroughly washed with distilled water, ultrasonically treated in water, separated by centrifugation, and then dried in an oven under $N_2$. The specific Brunauer-Emmett-Teller (BET) surface areas were determined to be >250 $m^2/g$. The $TiO_2$ particles (0.1 g) dispersed in an $CH_3CN$/tert-butanol solution of Dye (15 μmol) were allowed to stand overnight under stirring and then subjected to centrifugation. The collected particles were washed with the solvent and then dried in an oven under $N_2$. Similar procedures were applied to the deposition of ReP and CoP on the Dye-deposited $TiO_2$ powders.

Figure 3:
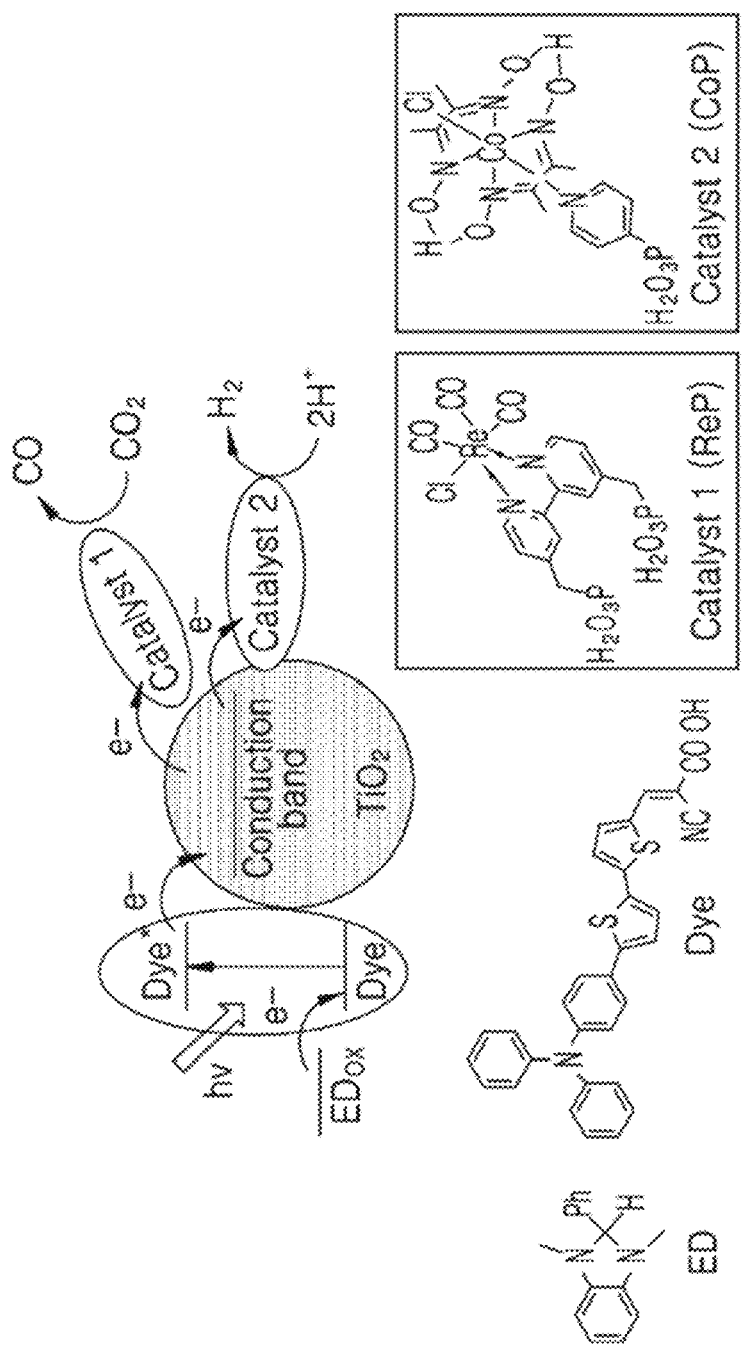
FIG. 3 is a schematic representation of a heterogeneous ternary photocatalytic system for syngas production.
Figure 4:
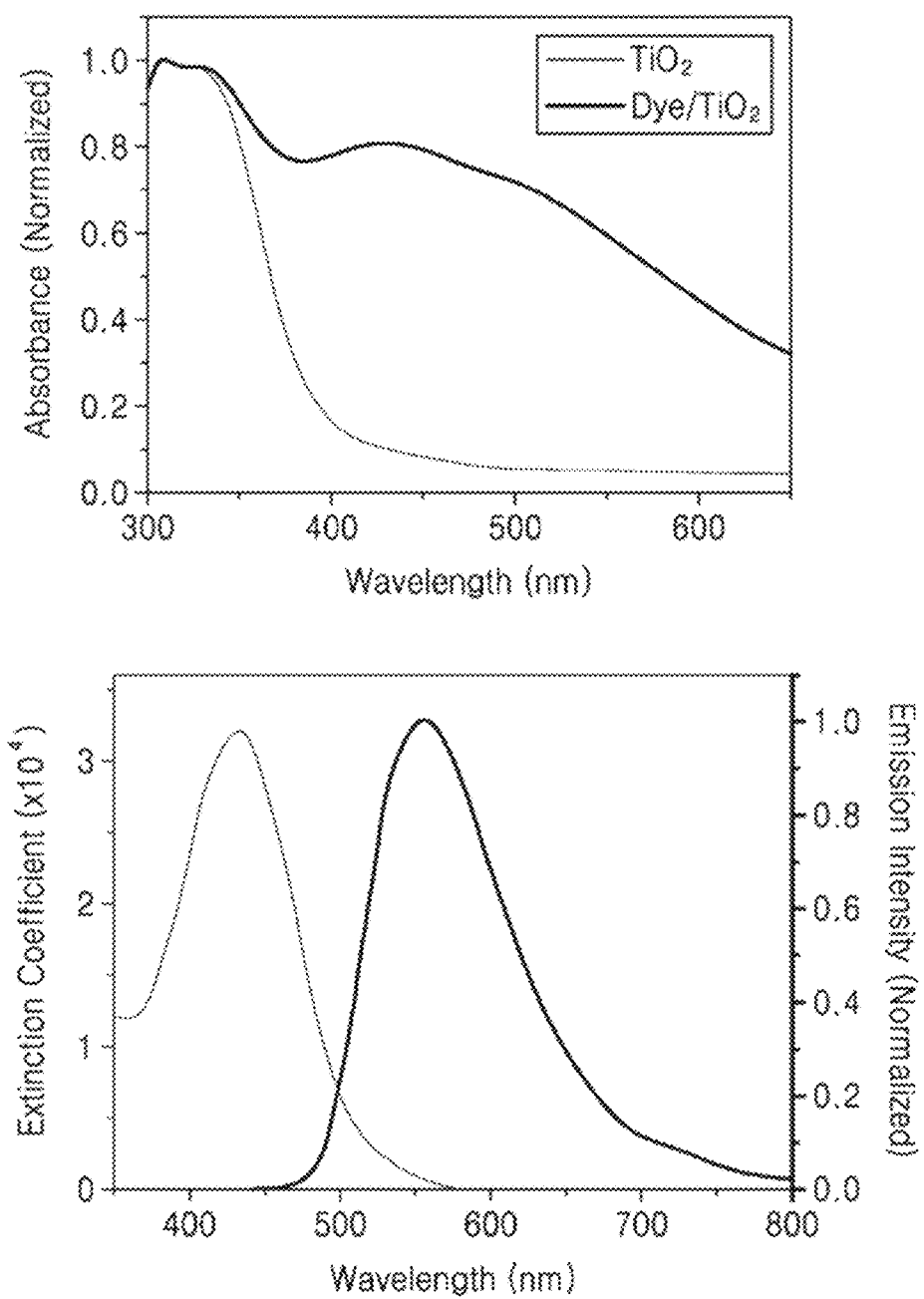
FIG. 4 shows diffuse-reflectance spectra (up) and UV-vis absorption spectra and photoluminescence spectra (down)
Figure 5:
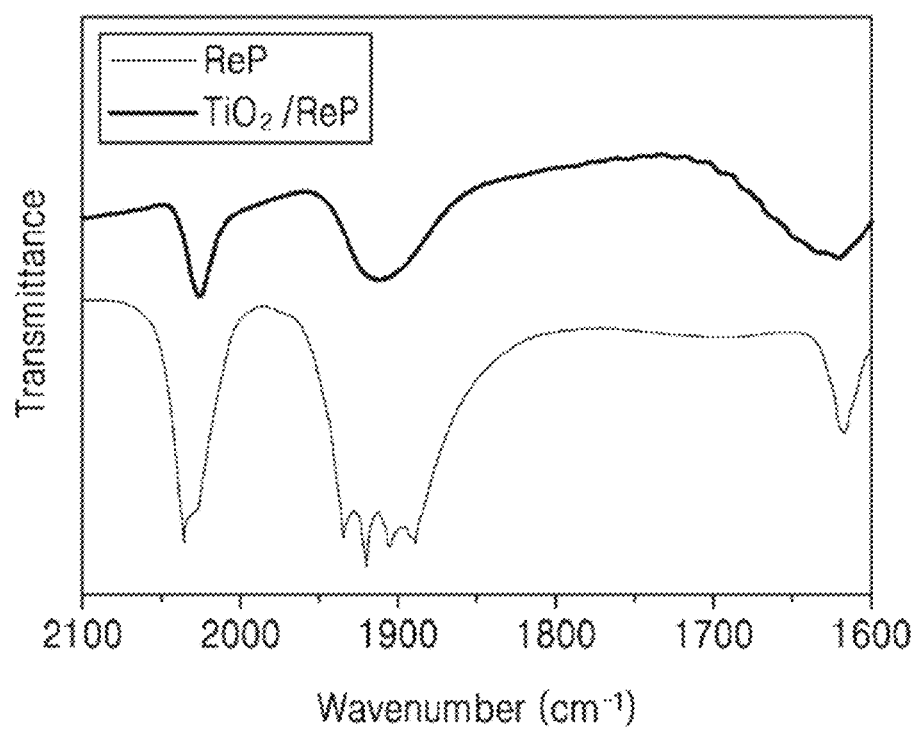
FIG. 5 shows IR spectra of Re(I) complex (ReP) and TiO$_2$/ReP.
Figure 6:
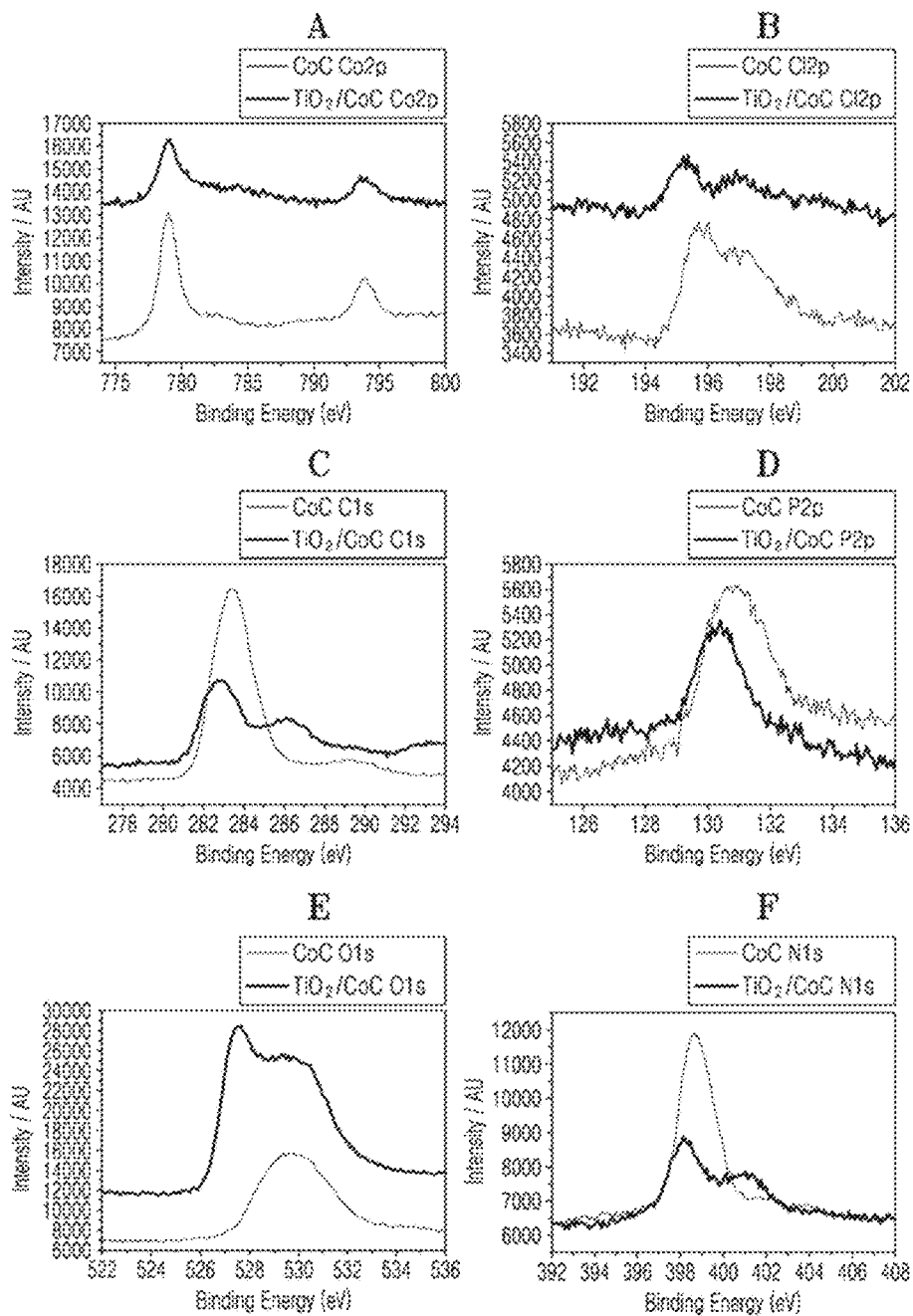
FIG. 6 shows XPS spectra of Co(III) molecular catalyst (CoP) and TiO$_2$/CoP: Co2p (a), Cl2p (b), C1s (c), P2p (d), O1s (e), and N1s (f)

Specifically, a $TiO_2$ hybrid system with an antenna and two transition-metal complex catalysts was prepared (FIG. 3). The antenna is (E)-2-cyano-3-(5'-(5''-(p-(diphenylamino) phenyl)thiophen-2''-yl)thiophen-2'-yl)-acrylic acid (Dye), catalyst 1 (ReP) is fac-[Re(4,4'-bis(diethoxyphosphorylmethyl)-2,2'-bipyridine)$(CO)_3$Cl], catalyst 2 (CoP) is [$Co^{III}$Cl (dimethylglyoximato)$_2$(pyridyl-4-phosphonic acid)]$^-$, and the sacrificial electron donor (SED) is 1,3-dimethyl-2-phenyl-1,3-dihydrobenzimidazole. These compounds were synthesized according to the literature methods (E. G. Ha et al., Chem. Commun. 50:4462-4, 2014; F. Lakadamyali et al., Chem. Commun., 47:1695-7, 2011; K. R. Justin Thomas et al., Chem. Mater., 20:1830-40, 2008; X. Q. Zhu et al., J. Am. Chem. Soc., 130:2501-16, 2008). The hybrid catalyst was prepared by anchoring Dye, ReP, and CoP on $TiO_2$ particles (Hombikat) in this sequence. Successful anchoring of the components was confirmed by diffuse-reflectance spectroscopy, IR-absorption spectra, and X-ray photoelectron spectroscopy (XPS) of the treated particles (FIGS. 4 to 6). In each anchoring procedure, the supernatant separated by centrifugation of the treated dispersion was virtually transparent. Therefore, the amount of each component anchored on $TiO_2$ was estimated to approximately equal that fed.

EXAMPLE 3

Photocatalytic CO and $H_2$ Production

Suspensions of Dye/$TiO_2$/ReP:CoP particles (10 mg with 1.5 μmol dye and 0.1 μmol ReP:CoP) in 3 mL DMF/water (0-20 vol %) containing SED (0.1 M) were placed in a Pyrex cell (1 cm pass length; 6.0 mL total volume), bubbled with $CO_2$ for 30 min, and sealed with a septum. A series of samples were set on a homemade merry-go-round apparatus and then irradiated under magnetic stirring with a LED lamp (λ>400 nm, 60 W, model Fc-6051, Cree Inc.). The amounts of CO and $H_2$ evolved in the overhead space of the cell were determined by gas chromatography (HP6890A GC equipped with a TCD detector) using a SUPELCO Carboxen™ 1010 PLOT Fused Silica Capillary column. The apparent quantum yield φ (CO and $H_2$) for CO and $H_2$ production was determined for the Dye/$TiO_2$/ReP:CoP (5:5) suspensions, a bandpass filter (420-450 nm) was used to isolate the 436 nm light form the emission light of a high-pressure mercury lamp (1000 W, model 6171, Newport Corporation), and the incident light flux was determined by using a 0.2 M ferrioxalate actinometer solution (A. M. Braun et al., Photochemical Technology; Wiley&Sons: New York, 76-80, 1991).

EXAMPLE 4

CO and $H_2$ Formation on the Variation of Water Contents

Figure 7:
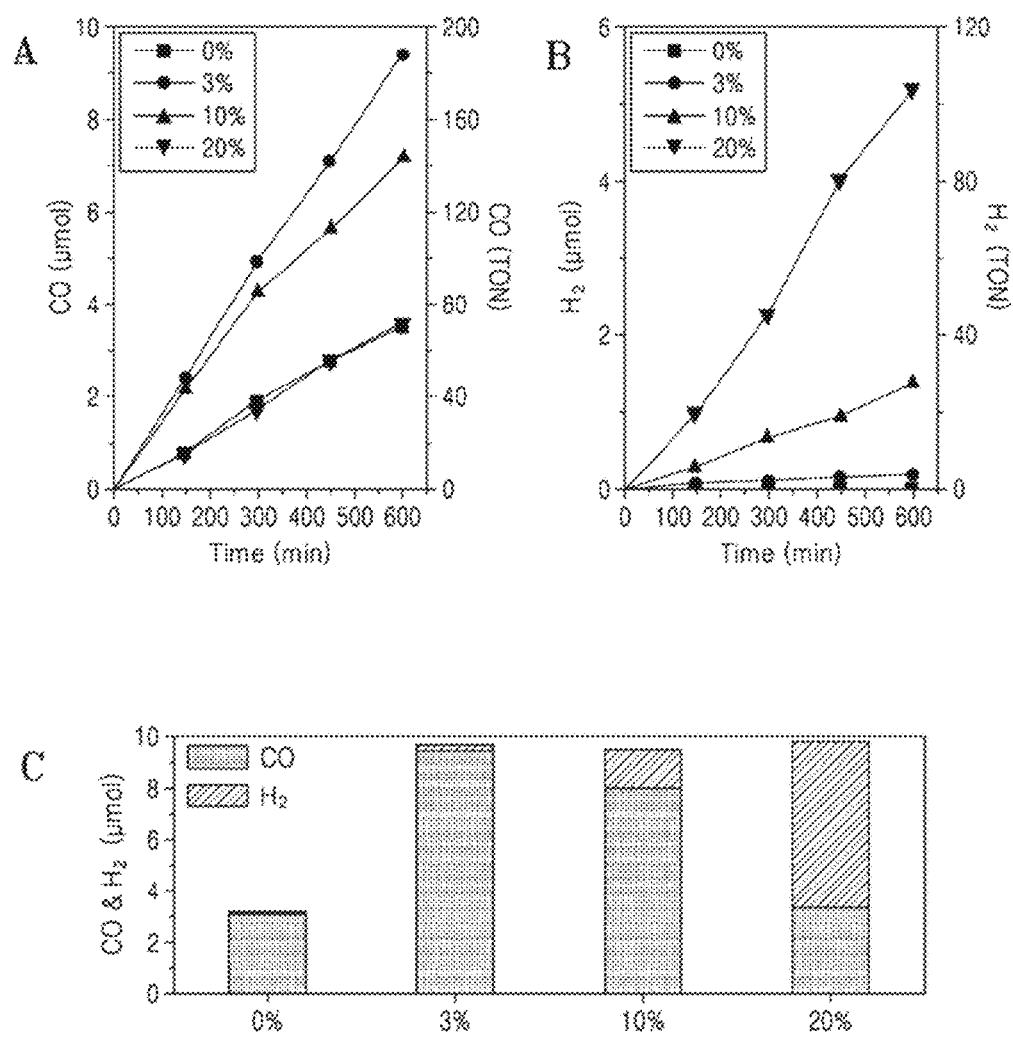
FIG. 7 shows plots of CO (a) and H$_2$ (b) formation versus irradiation time for 10 mg Dye/TiO$_2$/ReP (0.05 μmol):CoP (0.05 μmol) in 3 mL of DMF/H$_2$O mixture solvent containing 0.1 M SED: water contents (vol %)=0% (black squares), 3% (red circles), 10% (green triangles), and 20% (blue reverse triangles), $H_2/CO$ formation (μmol) on the variation of water contents (0-20 vol %) in $DMF/H_2O$ mixture solvent (c)
Figure 8:
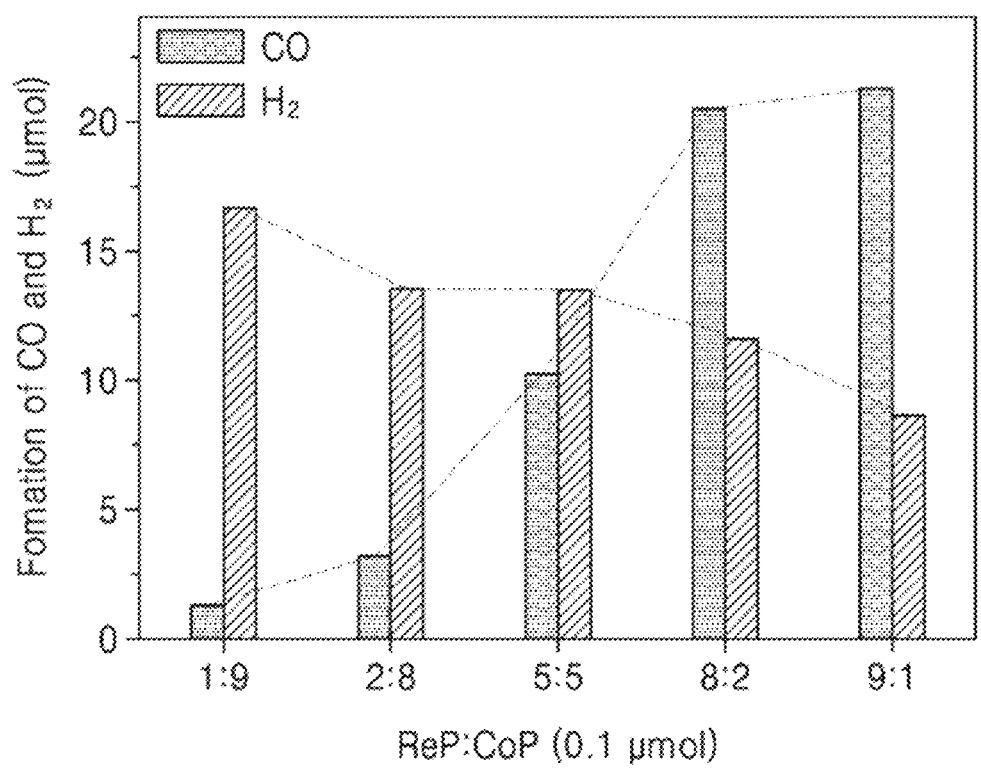
FIG. 8 shows dependences of $H_2/CO$ formation on molar ratios of ReP and CoP anchored on $TiO_2$; irradiation of 10 mg Dye/$TiO_2$/ReP:CoP (total 0.1 μmol) and 0.1 M SED in 3 mL $DMF/H_2O$ mixture solvent (20 vol % water) for 20 h.
Figure 9:
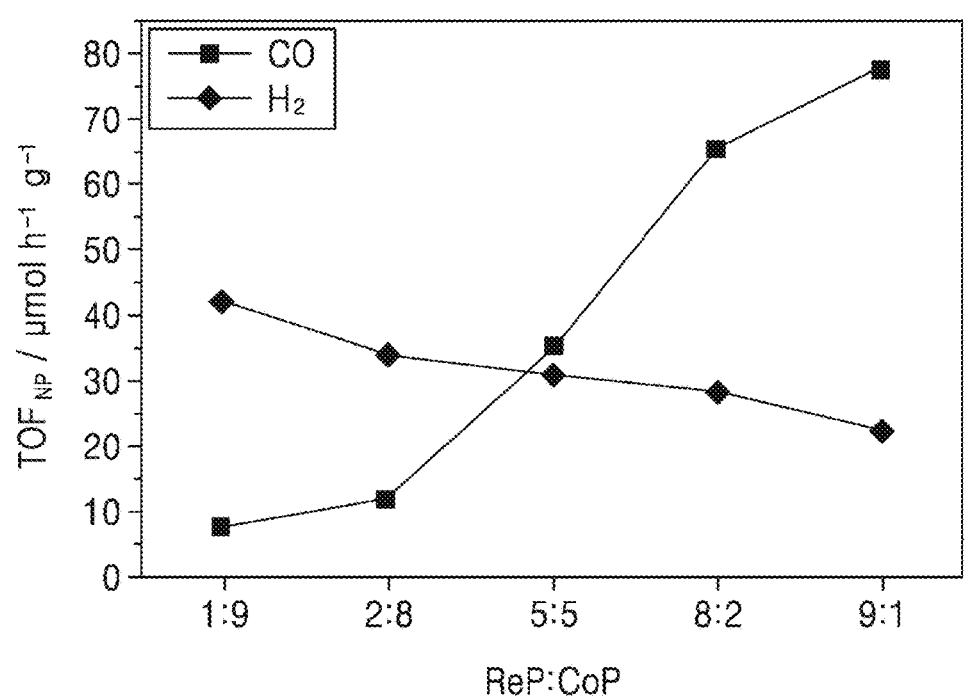
FIG. 9 shows CO and $H_2$ evolution rates per particle'

The formation of CO and $H_2$ for a hybrid system of 0.05 μmol ReP/0.05 μmol CoP grafted on 10 mg $TiO_2$ in the presence of various amounts of water (0 to 20 vol %) was confirmed (FIG. 7). The maximum amount of water in DMF-water mixed solvent system is limited to 20 vol % due to the poor solubility of the electron donor in water. Experimentally, the dissolved ED began to be insoluble at 20 vol % water. The efficiency of CO formation increased to a maximum in the presence of 3% water, but decreased at higher contents of water. In contrast, while the $H_2$ formation was negligible in the absence of water and still very small in the presence of 3% water, the $H_2$ production activity dramatically increased in the presence of 10% water and still more at 20 vol % water. It was found that the $H_2$/CO ratio can be further controlled by changing the ratio of ReP:CoP grafted on $TiO_2$ while fixing the total amount at 0.1 μmol. Upon changing the anchoring ratio of CoP and ReP from 9:1 to 1:9, the $H_2$:CO ratio is systematically tuned from 1:2 to 15:1 (FIG. 8). The turnover frequency (TOF) and number (TON) of CO and $H_2$ evolution per molecular catalyst (ReP or CoP) and per $TiO_2$ nanoparticle were determined (Table 1 and FIG. 9). The apparent quantum yields (AQY) of CO and $H_2$ formation for the hybrid systems (Dye/$TiO_2$/ReP: CoP (1:9 to 9:1)) in the presence of 20 vol % water were determined in a linear time-conversion region (Table 1).

TABLE 1

| Dye/$TiO_2$/ReP:CoP | (CO)/μmol (10 h) | $TON_{ReP}$ (10 h) | $TOF_{ReP}$ (10 h)$h^{-1}$ | AQY/CO | ($H_2$)/μmol (10 h) | $TON_{CoP}$ (10 h) | $TOF_{CoP}$ (10 h)$h^{-1}$ | AQY/$H_2$ |
|---|---|---|---|---|---|---|---|---|
| ReP:CoP (0.01:0.09 μmol) | 0.74 | 74 | 7.4 | $(9.2 \pm 0.3) \times 10^{-4}$ | 4.19 | 47 | 4.7 | $(6.1 \pm 0.2) \times 10^{-3}$ |
| ReP:CoP (0.02:0.08 μmol) | 1.16 | 58 | 5.8 | $(1.0 \pm 0.2) \times 10^{-3}$ | 3.37 | 42 | 4.2 | $(5.3 \pm 0.2) \times 10^{-3}$ |
| ReP:CoP (0.05:0.05 μmol) | 3.48 | 70 | 7.0 | $(2.6 \pm 0.1) \times 10^{-3}$ | 3.09 | 62 | 6.2 | $(4.2 \pm 0.2) \times 10^{-3}$ |

TABLE 1-continued

| Dye/TiO$_2$/ReP:CoP | (CO)/μmol (10 h) | TON$_{ReP}$ (10 h) | TOF$_{ReP}$ (10 h)h$^{-1}$ | AQY/CO | (H$_2$)/μmol (10 h) | TON$_{CoP}$ (10 h) | TOF$_{CoP}$ (10 h)h$^{-1}$ | AQY/H$_2$ |
|---|---|---|---|---|---|---|---|---|
| ReP:CoP (0.08:0.02 μmol) | 6.49 | 81 | 8.1 | (3.7 ± 0.2) × 10$^{-3}$ | 2.82 | 141 | 14.1 | (3.2 ± 0.2) × 10$^{-3}$ |
| ReP:CoP (0.09:0.01 μmol) | 7.73 | 86 | 8.6 | (4.6 ± 0.2) × 10$^{-3}$ | 2.21 | 221 | 22.4 | (2.7 ± 0.3) × 10$^{-3}$ |
| RuP/TiO$_2$/CoP | — | — | — | | 5.66(4 h) | 56.6(4 h) | 44.0(1 h)h$^{-1}$ | |
| RuP/TiO$_2$/CoP | — | — | — | | 0.24(4 h) | 2.4(4 h) | 0.6(1 h)h$^{-1}$ | |
| RuP/TiO$_2$/CoP | — | — | — | | 1.23(4 h) | 12.3(4 h) | 10.3(1 h)h$^{-1}$ | |

AQY (apparent quantum yield) = 2 × amount of H$_2$ or CO generated per unit time/number of incident photons per unit time

EXAMPLE 5

Confirmation of Persistency of Photocatalytic Activity

Figure 10:
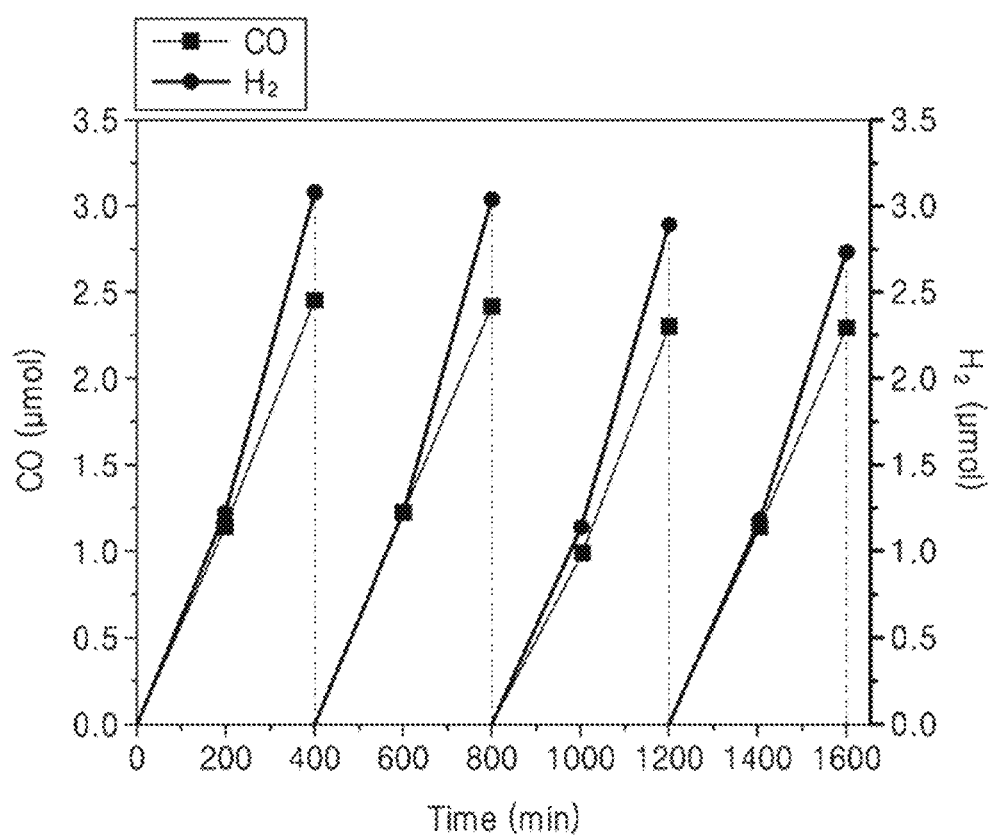
FIG. 10 shows the formation of CO and $H_2$ in a 4-cycle repetition at >400 nm for 400 min after $CO_2$ bubbling for 30 min in the dark (10 mg Dye (1.5 μmol)/$TiO_2$/ReP (0.05 μmol):CoP (0.05 μmol) in 3 mL $DMF/H_2O$ mixture solvent (20 vol % water) containing 0.1 M SED)
Figure 11:
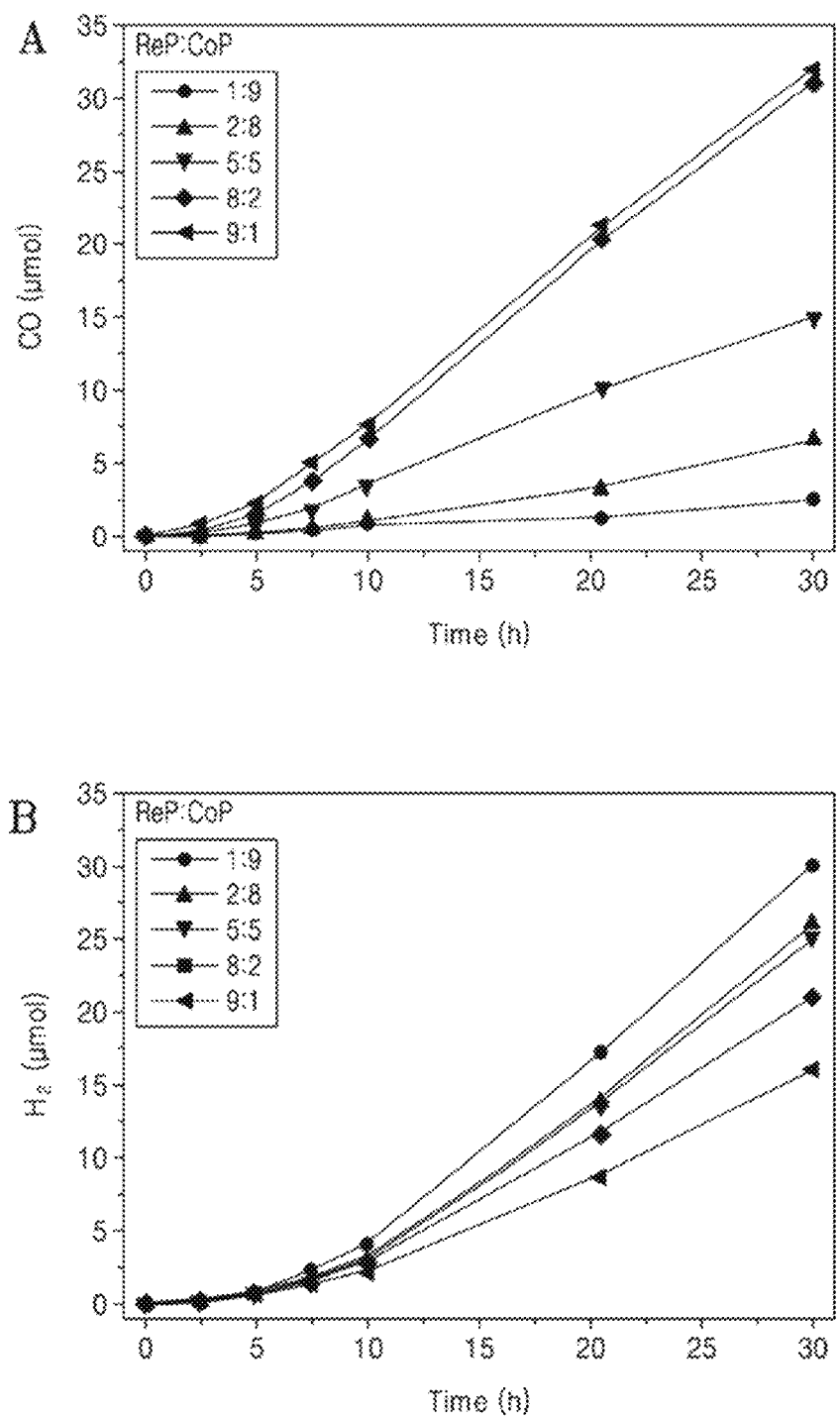
FIG. 11 shows plots of CO (a) and $H_2$ (b) formation versus time for Dye/$TiO_2$/ReP:CoP with different loading ratio of catalysts (1:9 to 9:1)
Figure 12:
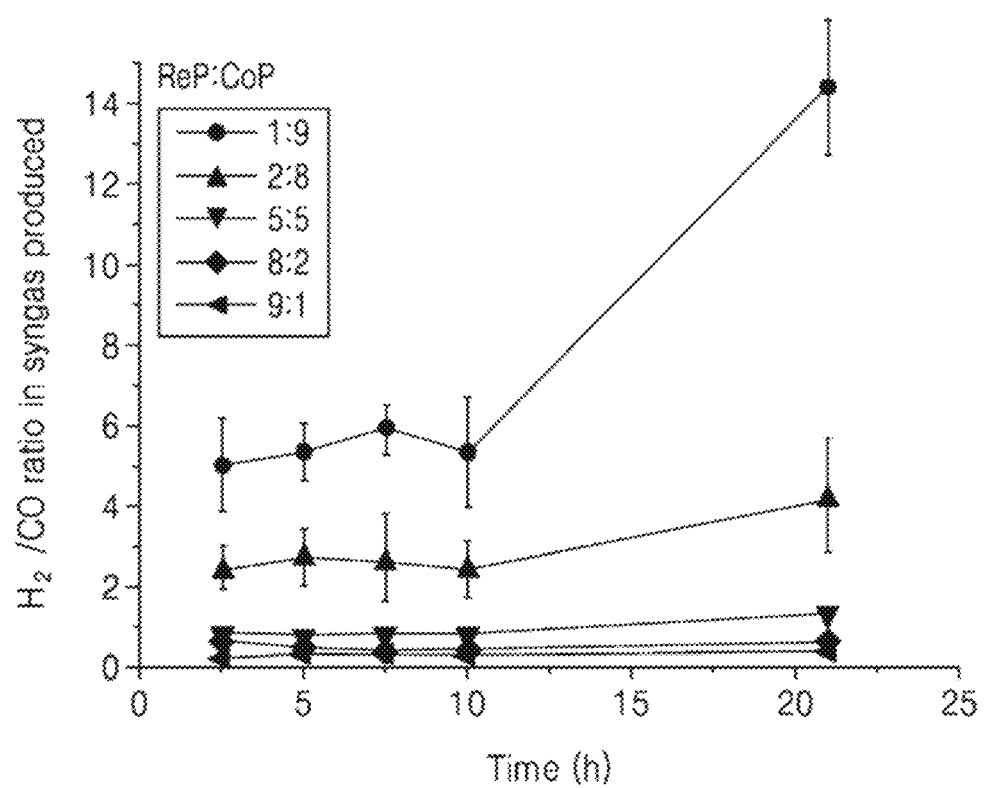
FIG. 12 shows plots of produced syngas composition ($H_2$/CO) versus irradiation time for Dye/$TiO_2$/ReP:CoP prepared with different loading ratio of ReP and CoP (1:9 to 9:1)

In order to confirm the persistency of photocatalytic activity, repetitive irradiation experiments were performed. No significant leveling-off tendency was observed in each cycle and the activity of syngas (CO and H$_2$) production was almost constant even with the extended catalytic cycles from 1st run to 4th run (FIG. 10). Overall the photocatalytic activities for CO and H$_2$ production in the inventive hybrid systems prepared are continuously increased up to 30 h with no appreciable leveling off tendency (FIG. 11). The initial gas compositions (H$_2$/CO ratio) are invariable during 10 hour reaction time. However, hydrogen evolution was a dominant feature in the extended reaction time (see FIG. 12 and Table 2).

TABLE 2

| Entry | System | ReP [μmol] | CoP [μmol] | H$_2$/CO @5 hours | H$_2$/CO @10 hours | H$_2$/CO @20 hours |
|---|---|---|---|---|---|---|
| 1 | Dye/TiO$_2$/ReP:CoP(1:9) | 0.01 | 0.09 | 5.3 | 5.3 | 14.5 |
| 2 | Dye/TiO$_2$/ReP:CoP(2:8) | 0.02 | 0.08 | 2.7 | 2.4 | 4.2 |
| 3 | Dye/TiO$_2$/ReP:CoP(5:5) | 0.05 | 0.05 | 0.8 | 0.8 | 1.3 |
| 4 | Dye/TiO$_2$/ReP:CoP(8:2) | 0.08 | 0.02 | 0.4 | 0.4 | 0.6 |
| 5 | Dye/TiO$_2$/ReP:CoP(9:1) | 0.09 | 0.01 | 0.3 | 0.3 | 0.4 |

EXAMPLE 6

Electron Transfer in Syngas Production

Figure 13:
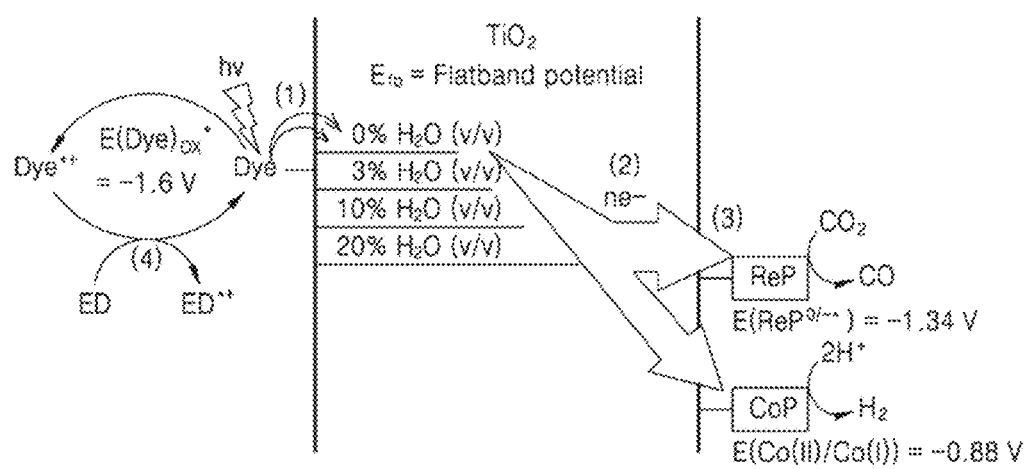
FIG. 13 is a schematic representation of electron transfer processes in visible-light induced syngas production by a dual molecular catalytic hybrid system, involving (1) electron injection from excited-state Dye into $TiO_2$ as the initiation process, (2) competitive transfer of the injected electrons to the ReP and CoP catalyst sites through $TiO_2$, and (3) the chemical processes proceeding on the ReP site ($CO_2$ reduction) and on the CoP site ($H_2$ evolution) under supply of electrons from $TiO_2$. (4) shows that this photocatalytic cycle for syngas production can be closed after the recovery of Dye by the reduction of Dye$^{\bullet+}$ with SED.
Figure 14:
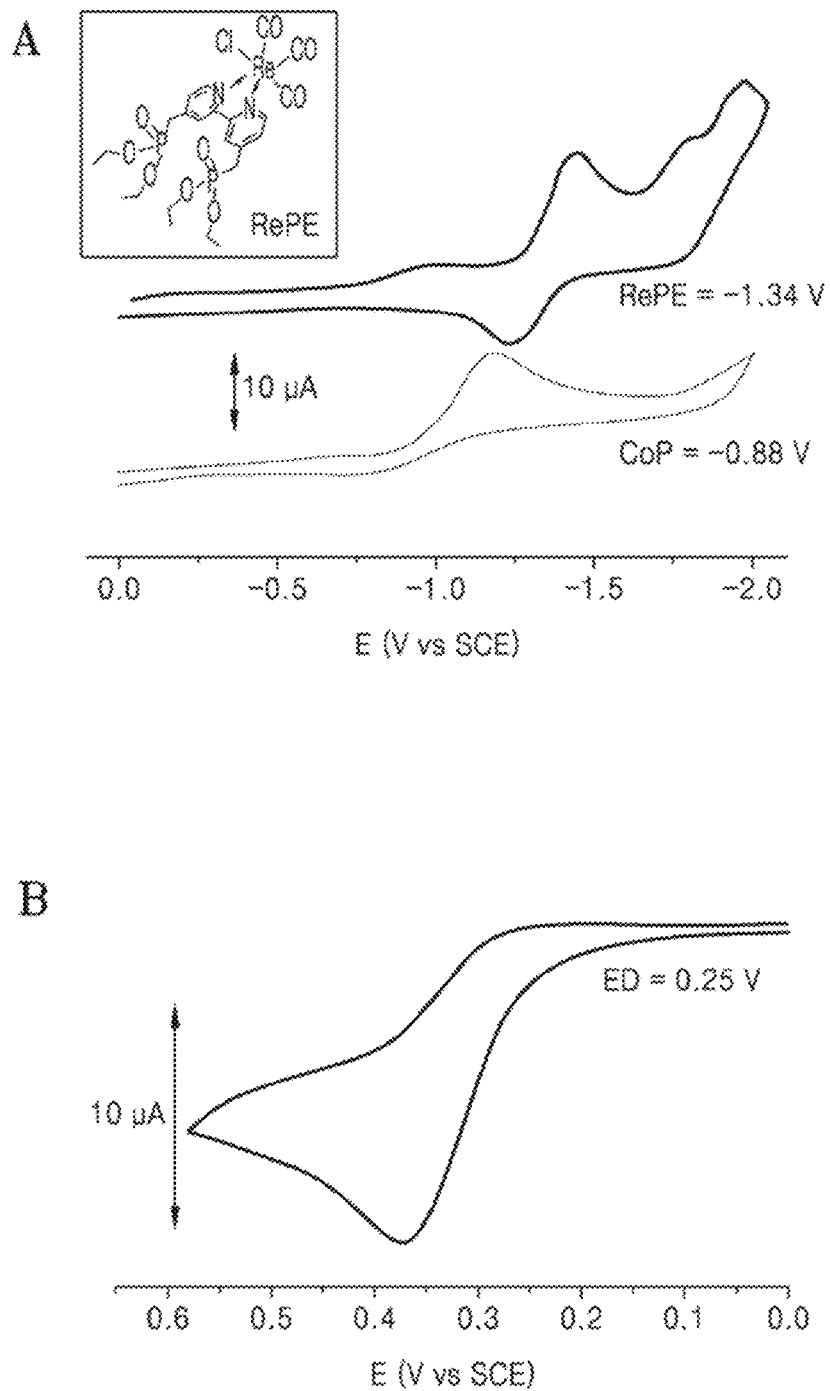
FIG. 14 shows cyclic voltammograms of CoP/RePE (a) and SED (BIH) (b)

The photocatalytic reaction of syngas involves electron injection from excited-state Dye into TiO$_2$ as the initiation process (W. S. Han et al., Chem. Eur. J, 18:15368-81, 2012), competitive transfer of the injected electrons to the ReP and CoP catalyst sites through TiO$_2$, and the chemical processes proceeding on the ReP site (CO$_2$ reduction) and on the CoP site (H$_2$ evolution) under supply of electrons from TiO$_2$. This photocatalytic cycle for syngas production can be closed after the recovery of Dye by the reduction of Dye$^{\cdot+}$ with SED (FIG. 13). The ratio of CO and H$_2$ formed should primarily depend on the relative rates of electron supply from TiO$_2$ to the two catalysis sites, which would be determined by the relationship between the reduction potentials of ReP and CoP with respect to the conduction-band edge of TiO$_2$. The reduction potential of CoP is −0.88 V vs SCE (F. Lakadamyali et al., Chem. Eur. J., 18:15464-74, 2012), significantly less negative than that of ReP (RePE, −1.34 V vs SCE) (D. I. Won et al., J. Am. Chem. Soc., 137:13679-90, 2015) (FIG. 14) (FIG. 14).

EXAMPLE 7

Flat-Band Potentials ($E_{fb}$) on the Variation of Water Contents

Figure 15:
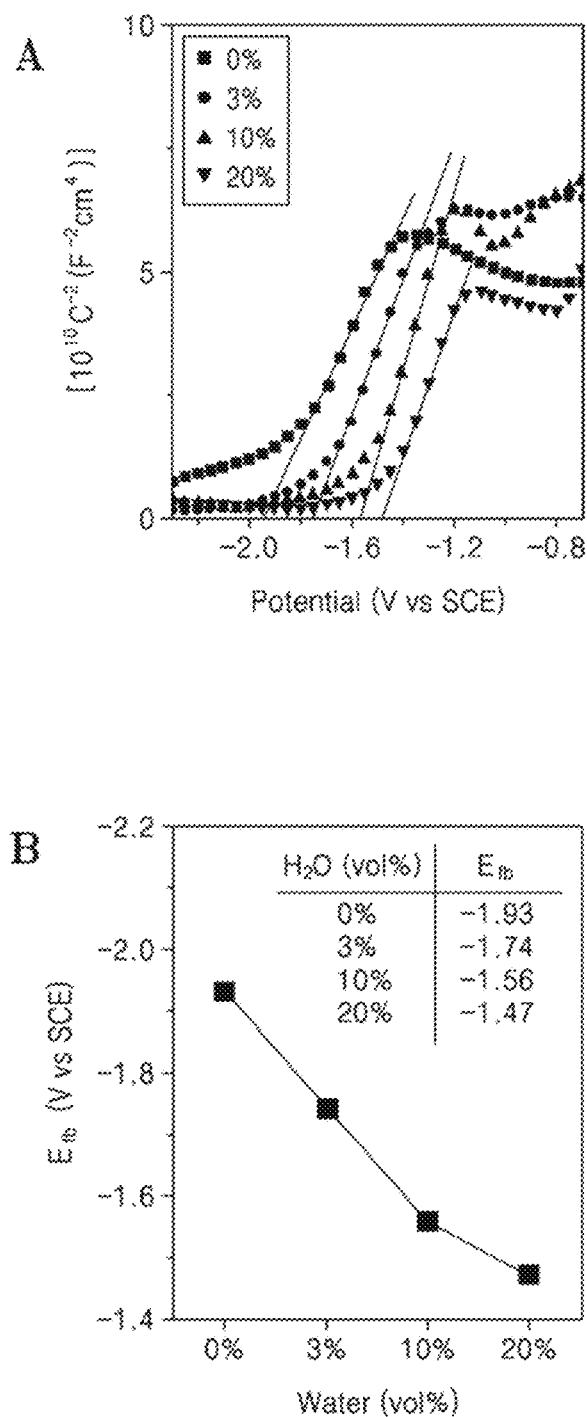
FIG. 15 shows Mott-Schottky plots (a) and flat-band potentials ($E_{fb}$) (b) for $TiO_2$ nanoparticle films on FTO electrode in the absence of water and in the presence of 3 vol %, 10 vol %, and 20 vol % water in acetonitrile containing 0.1 M TBAP.

The flat-band potential ($E_{fb}$) of TiO$_2$, which has been used as a practical measure of the conduction-band edge, is known to depend on solvents (G. Redmond et al., J. Phys. Chem., 97:1426-30, 1993). In a previous paper (D. I. Won et al., J. Am. Chem. Soc., 137:13679-90. 2015), the present inventors reported that $E_{fb}$ positively shifts in the presence of water in DMF. FIG. 15 shows four different Mott-Schottky (MS) plots taken for TiO$_2$ nanoparticle films in the absence of water and in the presence of 3, 10, and 20 vol % water in acetonitrile. The increase of added water resulted in substantial positive shifts of $E_{fb}$ from −1.93 V at 0% H$_2$O, to −1.74 V (3% H$_2$O), to −1.56 V (10% H$_2$O), and to −1.47 V (20% H$_2$O).

Figure 16:
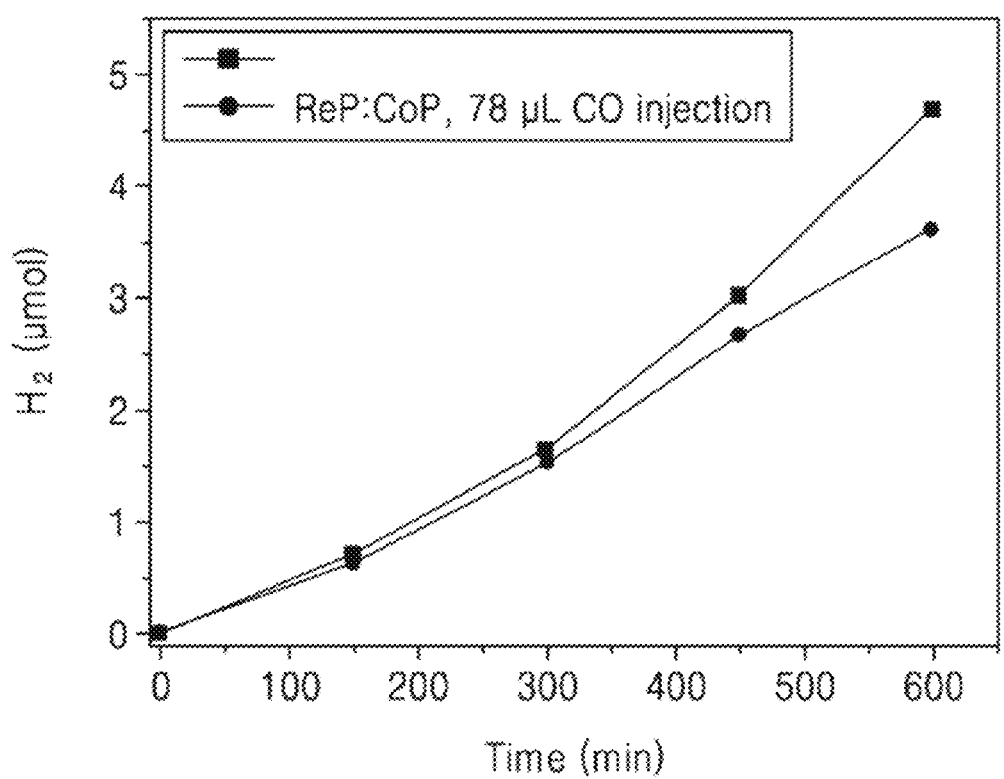
FIG. 16 shows plots of $H_2$ formation versus time for Dye (1.5 μmol)/$TiO_2$ (10 mg)/ReP (0.05 μmol):CoP (0.05 μmol) with addition of CO (78 μL) (red circles) and without addition of CO (black squares) in $CO_2$-saturated DMF-$H_2O$ mixture solvent (20 vol % water) containing 0.1 M SED.

Provided that the $E_{fb}$ values observed for the TiO$_2$ nanoparticle films can be applied to those of the TiO$_2$ hybrid particle dispersions in DMF, the electron transfer from TiO$_2$ to either ReP and CoP should be exergonic enough to proceed under the reaction conditions (A. Reynal et al., Ebergy Envrion. Sci., 6:3291-300, 2013; F. Lakadamyali et al., Chem. Eur. J., 18:15464-74, 2012; D. I. Won et al., J. Am. Chem. Soc., 137:13679-90, 2015). In fact, both CO and H$_2$ are generated in the presence of water (FIG. 7). It is of interest to note that the total amounts of CO and H$_2$ formed by irradiation of the TiO$_2$ hybrid catalyst with 0.05 μmol ReP: 0.05 μmol CoP in the presence of 3 to 20 vol % water are almost constant independently of the water contents while the H$_2$/CO ratios are variable with the water contents (FIG. 7). In this case, the total amounts of electrons utilized for the reductions of both CO$_2$ and H$_2$O would be constant but with different branch ratios of electron transfer depending on the water contents. The higher the water concentration, the faster the H$_2$-generation catalytic cycle should be completed to regenerate CoP. However, the ratios of the final products (CO and H$_2$) should be determined by complex factors, mainly by relative flows of both the first and second electrons to ReP and CoP and by efficiencies of the two-electron reduction catalytic cycles. The CO formation is dominant even in the presence of 10 vol % water (FIG. 7) where the concentration of $H_2O$ (5.6 M) is much higher than that of $CO_2$ (~0.2 M) (A. Gennaro et al., J. Electroanal. Chem., 289:203-15, 1990). A possible speculation is that electron supply from $TiO_2$ would more favorably occur to ReP than to CoP due to the different distances from the $TiO_2$ surface to the electron-accepting centers (the bpy ligand across the methylphosphonate spacer for ReP vs. $Co^{III}$ across the pyridylphosphonate bridge for CoP) as well as due to the different configurational situations of the anchored molecules (double anchoring with the two phosphonate groups of ReP vs. single anchoring of the one phosphonate substituent of CoP). Alternatively, the catalytic cycle on the ReP site would more efficiently proceed than that on the CoP site in the presence of 10 vol % water, even though the CO formation on ReP involves more complex chemical processes than the $H_2$ evolution on CoP. In the presence of 20 vol % water, however, the formation of $H_2$ is more efficient than that of CO, probably due to the large amount of water that should accelerate the chemical processes for the $H_2$ generation. Also, this behaviour may be supported by the $CO_2$ concentration lessened with higher water content (consequently lowering the catalytic CO formation efficiency) since the solubility of $CO_2$ gas is generally much lower in water (~0.034 M) than DMF solvent (~0.2 M) (A. Gennaro et al., J. Electroanal. Chem., 289: 203-15, 1990). The CO formation is sharply increased upon changing the anchoring amount of ReP from 0.01 µmol to 0.09 µmol, whereas the dependence of $H_2$ formation on the anchoring amount of CoP is not so remarkable (FIG. 8). In the presence of 20 vol % water, the catalytic cycle for $H_2$ generation would be efficient even with 0.01 µmol CoP enough to facilitate sufficient electron flow from $TiO_2$ to CoP in competition with the electron flow to 0.09 µmol ReP. This appears to be again true for the CO formation in cases where the anchoring amount of ReP is ≥0.05 µmol. The CO formation competes with or predominates over the $H_2$ generation even though the $CO_2$ concentration is much lower than the water concentration. The electron supply from $TiO_2$ to ReP and CoP might be dominated by a "seesaw mechanism" depending on the catalytic-cycle efficiencies under given reaction conditions. In addition, the poisoning of CoP catalyst by carbon monoxide should be considered as another reason of long-term instability of our photocatalytic system because the photocatalytic $H_2$ production by CoP proceeded in the presence of CO evolved from the co-catalyst ReP. In order to verify the negative effect of CO to the CoP complex during catalytic hydrogen production, the 78 µL CO gas (the amount of CO is equivalent to the amount of CO accumulated in the headspace (3 mL) of the reaction vessel with Dye/$TiO_2$/ReP:CoP (0.05 µmol:0.05 µmol) after 10 h of visible light illumination) was added to the reference condition (Dye/$TiO_2$/ReP (0.05 µmol):CoP (0.05 µmol)) before photoreaction; the resulting $H_2$ production activity were measured and compared with that without addition of CO. A slight reduction of $H_2$ production efficiency was observed in the photoreaction with addition of CO (FIG. 16), showing a negative influence of CO on catalytic $H_2$ generation (probably an inhibition of Co—H intermediate formation by CO coordination to the central Co metal site). However, overall the steady rise of $H_2$ production in the extended reaction period indicates that the CO poisoning effect is not a dominant feature in the inventive photocatalytic system probably due to the low solubility of CO in DMF solvent (FIG. 11).

While details of the present invention have been described above, it will be evident to those skilled in the art that such detailed descriptions are merely preferred embodiments and do not limit the scope of the present invention. Therefore, the true scope of the present invention should be defined by the appended claims and their equivalents.

What is claimed is:

1. A hybrid catalyst system comprising a hybrid catalyst comprising a semiconductor metal oxide, a dye, a rhenium (Re) catalyst, and a cobalt (Co) catalyst,
    wherein the dye, the rhenium (Re) catalyst, and the cobalt (Co) catalyst are grafted on the semiconductor metal oxide,
    wherein the rhenium (Re) catalyst is fac-[Re(4,4'-bis(diethoxyphosphoryl methyl)-2,2'-bipyridine)(CO)$_3$Cl],
    wherein the cobalt (Co) catalyst is $Co^{III}$Cl(dimethylglyoximato)$_2$(pyridyl-4-phosphonic acid),
    wherein the molar ratio of rhenium (Re) catalyst/cobalt (Co) catalyst is from 9:1 to 1:9.

2. The hybrid catalyst system according to claim 1, wherein the semiconductor metal oxide is $TiO_2$.

3. The hybrid catalyst system according to claim 1, further comprising a sacrificial reagent as an electron donor.

4. The hybrid catalyst system according to claim 1, further comprising a DMF/water mixture solvent.

5. The hybrid catalyst system according to claim 4, wherein the water content is 20% by volume or less.

6. The hybrid catalyst system according to claim 1, wherein the hybrid catalyst system produces hydrogen/carbon monoxide syngas.

7. The hybrid catalyst system according to claim 6, wherein the hybrid catalyst system enables control over the ratio of hydrogen/carbon monoxide.

8. The hybrid catalyst system according to claim 7, wherein the molar ratio of hydrogen/carbon monoxide is from 1:2 to 15:1.

9. The hybrid catalyst system according to claim 6, wherein the hydrogen/carbon monoxide syngas is produced under visible light irradiation.

* * * * *